United States Patent [19]

Preiss et al.

[11] Patent Number: 5,840,986
[45] Date of Patent: Nov. 24, 1998

[54] PREPARATION WITH HETEROGENEOUS CATALYSIS OF N-ALKYL-SUBSTITUTED AMINOALKYNES

[75] Inventors: Thomas Preiss, Ludwigshafen; Jochem Henkelmann, Mannheim; Joachim Wulff-Döring, Frankenthal; Susanne Stutz, Weinheim, all of Germany

[73] Assignee: BASF Aktiengesellschaft, Ludwigshafen, Germany

[21] Appl. No.: 923,557

[22] Filed: Sep. 4, 1997

[30] Foreign Application Priority Data

Sep. 5, 1996 [DE] Germany ............ 196 36 078.1

[51] Int. Cl.$^6$ .................................. C07C 209/26
[52] U.S. Cl. ................................ 564/471; 564/472
[58] Field of Search .......................... 564/471, 472

[56] References Cited

U.S. PATENT DOCUMENTS

| | | | |
|---|---|---|---|
| 3,496,232 | 2/1970 | Tedeschi et al. | 260/583 |
| 3,650,985 | 3/1972 | Kirchner et al. | 252/431 |
| 4,127,734 | 11/1978 | Fremont | 568/855 |
| 4,621,158 | 11/1986 | Hubert et al. | 564/473 |
| 5,300,716 | 4/1994 | Chapuis | 585/277 |

FOREIGN PATENT DOCUMENTS 080 794   6/1983   European Pat. Off. .

*Primary Examiner*—Brian M. Burn
*Attorney, Agent, or Firm*—Keil & Weinkauf

[57] ABSTRACT

A process for preparing N-alkyl-substituted aminoalkynes by reacting an alkyne with a carbonyl compound and an amine with heterogeneous catalysis in which an unsupported copper acetylide derived from malachite is used as the catalyst. The N-alkyl-substituted aminoalkyne have a wide variety of uses including their use as precursors for pharmaceuticals, their use in electroplating processes and their use as corrosion inhibitors.

22 Claims, No Drawings

PREPARATION WITH HETEROGENEOUS CATALYSIS OF N-ALKYL-SUBSTITUTED AMINOALKYNES

The present invention relates to a process with heterogeneous catalysis for preparing N-alkyl-substituted aminoalkynes in the presence of an unsupported catalyst.

N-Alkylaminoalkynes are important industrial intermediates with a wide range of uses. Some of them are used as precursors for pharmaceuticals, but they are also employed in electroplating and as corrosion inhibitors.

The preparation of N-alkyl-substituted aminoalkynes has been known for a long time and is utilized industrially. This generally entails reacting appropriately substituted alkynes, carbonyl compounds and amines in a Mannich-type condensation with homogeneous or heterogeneous catalysis.

Processes of this type with homogeneous catalysis are widely used and have been described many times. Thus, for example, CH-A-669 192 describes the preparation of pharmacologically active N-arylalkyl-substituted aminoalkynes in a reaction with homogeneous catalysis by copper and zinc salts such as CuCl or $ZnCl_2$.

DE-A-26 37 425 describes the preparation of dialkylamino-2-alkyn-4-ols by reacting formaldehyde, dialkylamine and an alkynol in aqueous acidic solution, preferably at a pH of 5, using a specific catalyst system, namely a combination of bromides, iodides or iodine which are soluble in the reaction mixture and soluble Cu(II) compounds. Carrying out the reaction with heterogeneous catalysis in the neutral or alkaline pH range is not suggested as a possible variant.

DE-B-1 100 617 likewise describes the preparation of dialkylamino-2-alkyn-4-ols by reacting formaldehyde, dialkylamine and an alkynol in aqueous acidic solution, preferably at a pH of 5 to 6 with homogeneous catalysis by copper sulfate, acetate, nitrate or chloride.

These processes have the known disadvantages associated with the removal of the homogeneous catalyst from the reaction mixture.

In addition, these processes cannot be used with volatile reactants such as, in particular, low-boiling alkynes.

On the other hand, the preparation of aminoalkynes using volatile reactants is distinctly more experimentally complicated.

U.S. Pat. No. 3,496,232 describes, for example, the preparation of propargylamines by the Mannich reaction. It is true that the catalysts generally described are unsupported or supported salts of metals of the first or second subgroup such as the chlorides, acetates and formates of copper. However, the reaction is preferably carried out with homogeneous catalysis by $CuCl_2$. The disadvantages of this process are that it is industrially elaborate, needing to be carried out with liquefied acetylene under high pressures (25 to 70 atm), and does not provide satisfactory yields of product.

It is true that U.S. Pat. No. 3,496,232 also mentions that copper acetylide catalysts can be used. Since these are prone to explosive decomposition, can be removed from the reaction solution by filtration only with difficulty and, moreover, catalyze the formation of cuprene, an acetylene polymerization product, these catalysts are not preferred.

For easiler manipulation of copper acetylides, they are applied to an inert carrier and mixed with a bismuth compound in order to reduce the formation of cuprene. However, use of such known catalysts for aminoalkylation of alkynes which are gaseous under the reaction conditions requires high partial pressures in order to achieve an approximately acceptable space-time yield. When working with acetylene, which is a thermally unstable gas which explodes easily even under atmospheric pressure, considerable safety measures are necessary in the design of the reactors for the pressure ranges required, which makes these processes economically disadvantageous.

Thus, for example, EP-A-0 080 794 describes a process with heterogeneous catalysis for preparing N,N-disubstituted propynylamines, the preferred catalysts employed being copper acetylides on a magnesium silicate carrier doped with bismuth oxide. The reaction takes place, for example, in a stirred autoclave with a suspended catalyst or in a fixed bed. This process has the disadvantage that the supported catalyst used is elaborate to prepare and has unsatisfactory activity because of its low copper content (about 5 to 35%). Reaction of acetylene in this case requires partial pressures of up to 20 or more atm. Because of the disadvantages described, an improved process for preparing aminoalkynes has been sought.

U.S. Pat. No. 3,650,985 describes the preparation of unsupported copper acetylide catalysts of the general formula $(CuC_2)w\ (CH_2O)x\ (C_2H_2)_y(H_2O)_z$ with $1 \leq w$, $x$, $y < 100$, preferably $w=4$, $x=0.24$ to 4, $y=0.24$ to 4 and $z=0.67$ to 2.8. These catalysts may additionally contain a bismuth compound and can be prepared by a particulate, water-insoluble copper compound, preferably basic copper carbonate, eg. synthetic malachite, being exposed simultaneously to formaldehyde and acetylene. They are used as aqueous catalyst suspension for the ethynylation of acetylenic hydrocarbons. Similar malachite catalysts are described in U.S. Pat. No. 3,560,576.

U.S. Pat. No. 4,127,734 describes the preparation of bismuth-modified, spherical malachites and their reaction with acetylene and formaldehyde to give unsupported ethynylation catalysts.

However, neither U.S. Pat. No. 3,650,985 nor U.S. Pat. No. 4,127,734 proposes using these specific catalysts in other reactions. In particular, there is no reference whatsoever to the possibility of using these catalysts for preparing aminoalkynes in nonaqueous medium.

It is an object of the present invention to provide a process for preparing N-alkyl-substituted aminoalkynes which no longer has the disadvantages of the prior art. In particular, it should be possible to carry out the novel process under pressures which are as low as possible. In addition, it should be possible by the process to prepare the required aminoalkynes in high yields and with high selectivity using a small amount of catalyst.

We have found that this object is achieved by providing a process in which an alkyne is reacted with a carbonyl compound and an amine in a reaction with heterogeneous catalysis by an unsupported copper catalyst which is derived from malachite.

It has furthermore been found, surprisingly, that the process according to the invention is, contrary to the skilled worker's expectation, also suitable for preparing aminoalkynes which are hydroxyalkyl-substituted on the nitrogen atom and/or on the alkyne carbon atom, although a whole series of side reactions is to be expected in this case. On use of mono- or di-hydroxyalkyl-substituted amines and a carbonyl compound, ring closure reactions must be expected, such as oxazolidine formation. This is particularly true on use of β-amino alcohols as amine component if alkaline reaction conditions are used in anhydrous solvents or in the presence of dehydrating agents, and not, as described in DE-A-26 37 425, in acidic aqueous solution. In addition, the formation of acetals from hydroxyalkyl-substituted reactants and the carbonyl compound is to be expected. These acetals have increased stability under alkaline reaction conditions. There may furthermore also be the formation of open-chain condensation products from a hydroxyalkyl-substituted alkyne, the amine component and an appropriate aldehyde. Surprisingly, it has additionally been found in this case that no special measures need be taken to adjust the pH; this is because the unwanted side reactions to be expected do not occur in the neutral to alkaline pH range preset by the reactants.

The present invention relates to a process for preparing N-alkyl-substituted aminoalkynes of the formula I

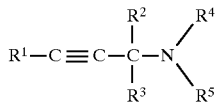

where
R$^1$ is hydrogen, alkyl, haloalkyl, cycloalkyl, aryl, alkoxy, alkoxyalkyl or hydroxyalkyl, preferably hydrogen, alkyl or hydroxyalkyl;

R$^2$ and R$^3$ are, independently of one another, hydrogen, alkyl, haloalkyl, aryl or alkoxy, with, in particular, at least one of the radicals, preferably both, being hydrogen;

R$^4$ and R$^5$ are, independently of one another, hydrogen, alkyl, haloalkyl, aryl, alkoxy or hydroxyalkyl, or R$^4$ and R$^5$ form, together with the nitrogen atom to which they are bonded, a 5- or 6-membered heterocyclic ring, with, in particular, at least one, preferably both, radicals being hydrogen, alkyl or hydroxyalkyl;

wherein a mixture of an alkyne of the formula II

where
R$^1$ has the abovementioned meanings, a carbonyl compound of the formula III

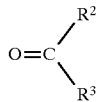

where
R$^2$ and R$^3$ have the abovementioned meanings, and an amine of the formula IV

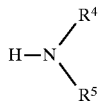

where
R$^4$ and R$^5$ have the abovementioned meanings, is reacted with heterogeneous catalysis, wherein an unsupported copper catalyst which is derived from malachite (CuCO$_3$.Cu(OH)$_2$) is used. The catalyst is preferably employed in activated form, eg. as copper acetylide catalyst. It is furthermore conceivable to use other alkynes or alkynols for the activation in place of acetylene.

For the purpose of the present invention, halogen is fluorine, chlorine, bromine and iodine and, in particular, chlorine and bromine.

The term "alkyl" embraces straight-chain and branched alkyl groups. These are preferably straight-chain or branched C$_1$–C$_{12}$-alkyl and, in particular, C$_1$–C$_6$-alkyl groups. Examples of alkyl groups are, in particulars methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl and dodecyl.

Haloalkyl is an alkyl group as defined above which is halogenated with one or more halogen atoms, in particular chlorine and bromine, partly or completely, preferably with one to three halogen atoms.

The above statements on the alkyl group and haloalkyl group apply correspondingly to the alkyl group in alkoxy, alkoxyalkyl and hydroxyalkyl radicals.

Cycloalkyl is preferably C$_3$–C$_8$-cycloalkyl such as cyclopropyl, cyclobutyl, cyclopentyl, cyclohexyl, cycloheptyl or cyclooctyl, or cyclopentylmethyl, cyclopentylethyl and cyclohexylmethyl and cyclohexylethyl.

Aryl is preferably phenyl or naphthyl.

R$^4$ and R$^5$ may form, together with the nitrogen atom to which they are bonded, a heterocyclic ring. Examples thereof are succinimido and phthalimido groups or an unsaturated or saturated 5- or 6-membered heterocyclic ring which may contain another heteroatom selected from S and N, preferably N. Examples thereof which may be mentioned are: piperidinyl, piperazinyl and tetrahydropyrimidinyl groups.

Preferably used in the process according to the invention are copper acetylide catalysts which additionally contain a bismuth compound such as (BiO)$_2$CO$_3$, Bi(NO$_3$)$_3$ or Bio(NO$_3$). Particularly preferred catalysts have about 40 to 70% by weight of Cu and about 0.1 to 10% by weight of Bi.

Catalysts of this type are known in the prior art and are described, for example, in U.S. Pat. No. 3,650,985, U.S. Pat. No. 3,560,576 and U.S. Pat. No. 4,127,734. The disclosure in these publications is incorporated herein by reference.

In a preferred embodiment of the present invention, the catalyst used comprises at least one copper acetylide complex of the formula V

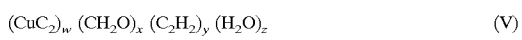

with 1≦w, x, y, z<100, and a bismuth compound.

The indices preferably hare the following values:
w 2 to 6, in particular 4,
x 0.24 to 4.00,
y 0.24 to 2.40,
z 0.67 to 2.8.

Processes for preparing these copper acetylide complexes which may be doped with Bi are likewise described in U.S. Pat. No. 3,650,985 and U.S. Pat. No. 4,127,734. In general, the copper acetylide complexes used according to the invention as unsupported heterogeneous catalysts are obtained by simultaneously reacting a copper compound selected from copper oxides, copper silicates, copper phosphates, copper hydroxides and basic copper carbonates, eg. natural and, preferably, synthetic maliachites, in the presence of a bismuth compound selected from bismuth oxide carbonate and bismuth nitrate, in the presence or absence of an alkali metal carbonate or bicarbonate, with formaldehyde and acetylene.

In a preferred embodiment of the process according to the invention, compounds in which at least one of the radicals $R^1$, $R^4$ or $R^5$ is hydroxyalkyl are prepared. Surprisingly, it is possible to prepare such hydroxyalkyl-substituted aminoalkynes without special measures to adjust the pH, namely in the neutral to alkaline pH range preset by the reactants, without the expected unwanted side reactions occuring.

In another preferred embodiment of the process according to the invention, compounds in which the radicals $R^2$ and $R^3$ in formula III are, independently of one another, hydrogen or alkyl are prepared. $R^2$ and $R^3$ are, in particular, both hydrogen.

It is furthermore preferred to react alkynes of the formula II where $R^1$ is hydrogen, alkyl or hydroxyalkyl.

The process according to the invention is particularly suitable for reacting alkynes of the formula II which are gaseous at the reaction temperature, such as acetylene, propyne, 1-butyne etc. Acetylene is preferably used. Reaction of these gaseous alkynes advantageously takes place at a lower pressure than in prior art processes, namely under a pressure of up to 3 bar, preferably up to 2 bar, and particularly, preferably under ambient pressure.

When acetylene is used as alkyne of the formula II, it is preferably neither compressed nor liquefied for the reaction. If low-boiling amines are used as amines of the formula IV, the reaction can, if required, be carried out under the autogenous pressure maintaining the pressure conditions described above.

If the compound of the formula II is an alkyne which is gaseous under the reaction conditions, specifically acetylene, the carbonyl compound of the formula III and the amine of the formula IV are introduced together with the unsupported heterogeneous catalyst, with or without a solvent, into a reactor provided with a mixing appliance. Suitable reactors are known to the skilled worker. They include the containers for reactions under pressure described in Ullmanns Enzyklopädie der technischen Chemie, 3rd edition, (1951) Volume 1, pages 117 et seq. and pages 769 et seq. The alkyne is preferably added beneath the level of the liquid reaction mixture, eg. with an immersion tube or a coiled tube which has orifices facing in or against the direction of flow of the reaction mixture. The rate of addition is limited by the abovementioned pressure ranges to be maintained.

The reaction can be carried out without solvent or in the presence of an organic solvent which is inert toward the reactants. Examples of suitable solvents are saturated cyclic ethers such as tetrahydrofuran and dioxane.

The reaction temperature can be chosen in the range from ambient temperature to the boiling point of the reaction mixture. The reaction is preferably carried out at from 20° to 200° C., preferably 30° to 180° C., particularly preferably 40° to 160° C.

The pH of the reaction is preset by the reactants and is in the neutral or alkaline pH range.

The process according to the invention for preparing N-alkyl-substituted aminoalkynes using said unsupported heterogeneous catalysts makes Mannich-type condensations possible with high selectivities and high yields.

The invention is illustrated by means of the following, non-restrictive examples.

EXAMPLES

Example 1

73 g (1 mol) of diethylamine were introduced with 30 g (1 mol) of paraformaldehyde and 100 ml of 1,4-dioxane into a 500 ml three-neck flask. Then 4.5 g of a copper catalyst activated with acetylene under atmospheric pressure (54% copper and 3% bismuth) were added to this solution. This solution was then heated to 50° C. and, at this temperature, acetylene was passed in at 6 l/hour for 24 hours. After the reaction was complete, N,N-diethylaminopropyne was obtained in 90% yield (based on amine/selectivity>95%).

EXAMPLE 2

129 g (1 mol) of di-n-buttylamine were introduced with 30 g (1 mol) of paraformaldehyde into a 500 ml three-neck flask. Then 4.5 g of a copper catalyst activated with acetylene under atmospheric pressure (54% copper and 3% bismuth) were added to this solution. This solution was then heated to 80° C. and, at this temperature, acetylene was passed in at 6 l/hour for 16 hours. After the reaction was complete, N,N-di-n-butylaminopropyne was obtained in 92% yield (based on amine/selectivity>95%).

We claim:

1. A process for preparing N-alkyl-substituted aminoalkynes of the formula I

where
  $R^1$ is hydrogen, alkyl, haloalkyl, cycloalkyl, aryl, alkoxy, alkoxyalkyl or hydroxyalkyl;
  $R^2$ and $R^3$ are, independently of one another, hydrogen, alkyl, haloalkyl, aryl or alkoxy;
  $R^4$ and $R^5$ are, independently of one another, hydrogen, alkyl, haloalkyl, aryl, alkoxy or hydroxyalkyl, or $R^4$ and $R^5$ form, together with the nitrogen atom to which they are bonded, a 5- or 6-membered heterocyclic ring;
wherein a mixture of an alkyne of the formula II

where
  $R^1$ has the abovementioned meanings, a carbonyl compound of the formula III

where
  $R^2$ and $R^3$ have the abovementioned meaning and an amine of the formula IV

where $R^4$ and $R^5$ have the abovementioned meanings, is reacted with heterogeneous catalysis, wherein an unsupported copper catalyst which is derived from malachite is used.

2. The process of claim 1, wherein the copper catalyst is a copper acetylide catalyst which additionally contains a bismuth compound.

3. The process of claim 1, wherein the catalyst contains 40–70% by weight of copper and 0.1–10% by weight of bismuth.

4. The process of claim 1, wherein the catalyst contains at least one copper acetylide complex of the formula V

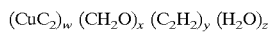 (V)

with $1 \leq w, x, y, z < 100$, and a bismuth compound.

5. A process as claimed in claim 4, wherein a complex of the formula V where w has a value from 2 to 6, x has a value from 0.24 to 4.00, y has a value from 0.24 to 2.40, and z has a value from 0.67 to 2.8, is used.

6. The process of claim 1, wherein the reaction is carried out under a pressure of up to 3 bar pressure.

7. The process of claim 1, wherein the reaction is carried out at from 20° to 200° C.

8. The process of claim 1, wherein the reaction takes place in the neutral or alkaline pH range.

9. The process of claims 1, wherein the reaction takes place without diluent.

10. The process of claim 1, wherein the reaction takes place in a nonaqueous medium.

11. The process of claim 1, wherein first the carbonyl compound of the formula III, the amine of the formula IV and the catalyst are introduced, and subsequently the alkyne of the formula II is added.

12. The process of claim 1, wherein an alkyne of the formula II where $R^1$ is hydrogen, alkyl or hydroxyalkyl is reacted.

13. The process of claim 12, wherein an alkyne which is gaseous at the reaction temperature is used as compound of the formula II.

14. The process of claim 13, wherein acetylene is used as compound of the formula II and is not compressed or liquefied for the reaction.

15. The process of claim 1, wherein an alkyne of the formula II and an amine of the formula IV, where at least one of the radicals $R^1$, $R^4$ or $R^5$ is hydroxyalkyl, are reacted.

16. The process of claim 1, wherein a carbonyl compound of the formula III where $R^2$ and $R^3$ are, independently of one another, hydrogen or alkyl, is reacted.

17. The process of claim 6, wherein the reaction is carried out under a pressure of up to 2 bar.

18. The process of claim 6, wherein the reaction is carried out at ambient pressure.

19. The process of claim 7, wherein the reaction is carried out at from 30° to 180° C.

20. The process of claim 7, wherein the reaction is carried out at from 40° to 160° C.

21. The process of claim 11, wherein the carbonyl compound, the amine and the catalyst are introduced with a solvent and subsequently the alkyne is added beneath the level of the liquid reaction mixture.

22. The process of claim 16, wherein both $R^2$ and $R^3$ are hydrogen.

* * * * *